(12) United States Patent
Adnot et al.

(10) Patent No.: US 8,614,247 B2
(45) Date of Patent: Dec. 24, 2013

(54) METHODS FOR PREVENTING, ATTENUATING OR TREATING PULMONARY HYPERTENSION USING A SEROTONIN TRANSPORTER INHIBITOR, AND PHARMACEUTICAL COMPOSITIONS FOR THE TREATMENT THEREOF

(75) Inventors: Serge Adnot, Saint-Maur-des-Fausses (FR); Saadla Eddahibi, Paris (FR)

(73) Assignees: Institut National de la Sante et de la Recherche Medicale, Paris (FR); Assistance Publique-Hopitaux de Paris, Paris (FR)

( * ) Notice: Subject to any disclaimer, the term of this patent is extended or adjusted under 35 U.S.C. 154(b) by 740 days.

(21) Appl. No.: 11/246,282

(22) Filed: Oct. 11, 2005

(65) Prior Publication Data

US 2006/0100270 A1    May 11, 2006

Related U.S. Application Data

(63) Continuation of application No. PCT/EP2004/004530, filed on Apr. 9, 2004.

(60) Provisional application No. 60/461,427, filed on Apr. 10, 2003.

(51) Int. Cl.
| | | |
|---|---|---|
| *A01N 43/08* | (2006.01) | |
| *A61K 31/34* | (2006.01) | |
| *A01N 33/02* | (2006.01) | |
| *A61K 31/135* | (2006.01) | |

(52) U.S. Cl.
USPC ............ 514/469; 514/649; 514/321; 549/467

(58) Field of Classification Search
USPC .......................... 514/469, 649, 321; 549/467
See application file for complete search history.

(56) References Cited

U.S. PATENT DOCUMENTS 5,910,319 A * 6/1999 Anderson et al. ............ 424/458

FOREIGN PATENT DOCUMENTS

WO    WO-00/56312 A1    9/2000

OTHER PUBLICATIONS

Marcos, E., et al. American Journal of Respiratory and Critical Care Medicine 2003, 168, 487-493.*
Keegan, A., et al. Circulation Research 2001, 89, 1231-1239.*
Eddahibi, S., et al. J. Clin. Invest. 2001, 108, 1141-1150.*
Hicks, M. N., et al. British Journal of Pharmacology 2002, 137, 938.*
Eddahibi (Circ Res, 1999, 84, 329-336).*
Eddahibi et al. (Eddahibi, S., et al. J. Lab. Clin. Med 2002, 108, 194-201).*
Eddahibi et al. (Eddahibi, S., et al, J of Clin Invest, 2000, 105, 11, p. 1555-62).*
MacLean Review (TiPS, 1999, 20, 490-95).*
Eddahibi et. al., The Journal of Pharmacology and Experimental Therapeutics, vol. 291, No. 1, 2001,pp. 148-154.
Eddahibi et al., Circulation Research, vol. 84, No. 3, 1999, pp. 329-336.
Tatarczynska et al., Polish Journal of Pharmacology, vol. 54, No. 6, ISSN: 1230-6002, 2002, pp. 615-623.
Dawson et al., Neuropharmacology, vol. 39, No. 6, 2000, pp. 1044-1052.
Eddahibi et al., The Journal of Clinical Investigation, vol. 105, No. 11, Jun. 2000 XP001197383, pp. 1555-1562.
Brenot et al., British Heart Journal, vol. 70, No. 6, 1993, pp. 537-541.
Choi et al., FEBS Letters, vol. 391 (1-2), 1996, pp. 45-51.
Lee et al., American Journal of Physiology, vol. 266 (1 Pt 1), 1994, pp. L46-52.
Lee et al., Circulation Research, vol. 68, No. 5, May 1991, pp. 1362-1368.
MacLean et al., British Journal of Pharmacology, vol. 119, 1996, pp. 917-930.
Ramamoorthy et al., Proc. Natl. Acad. Sc. USA, vol. 90, Mar. 1993, pp. 2542-2546.
Rubin, The New England Journal of Medicine, vol. 336, No. 2, Jan. 9, 1997, pp. 111-117.
DeJonghe et al., CNS Drugs, vol. 7, No. 6, 1997, pp. 452-467.
Nerve et al., The American Journal of Medicine, vol. 89, Jul. 1990, pp. 117-120.
Wagenvoort et al., Circulation, vol. 42, Dec. 1970, pp. 1163-1184.

* cited by examiner

*Primary Examiner* — Sreeni Padmanabhan
*Assistant Examiner* — Uma Ramachandran
(74) *Attorney, Agent, or Firm* — Birch, Stewart, Kolasch & Birch, LLP.

(57) ABSTRACT

The invention relates to a method for preventing, attenuating or treating pulmonary hypertension in an individual in need thereof, comprising administering at least one 5-HTT inhibitor to said individual.

7 Claims, 6 Drawing Sheets

5-HT receptor antagonists

Ketanserin  GR127935

Controls

5-HTT inhibitors

Citalopram  Fluoxetine

METHODS FOR PREVENTING, ATTENUATING OR TREATING PULMONARY HYPERTENSION USING A SEROTONIN TRANSPORTER INHIBITOR, AND PHARMACEUTICAL COMPOSITIONS FOR THE TREATMENT THEREOF

This application is a Continuation of copending PCT International Application No. PCT/EP2004/004530 filed on Apr. 9, 2004, which designated the United States, and on which priority is claimed under 35 U.S.C. §120. This application also claims priority under 35 U.S.C. §119 (e) on Patent Application No. 60/461,427 filed in the United States of America on Apr. 10, 2003. The entire contents of each of the above documents is hereby incorporated by reference.

FIELD OF THE INVENTION

The present invention pertains to the field of therapy of pulmonary hypertension, and is based on a novel therapeutic approach for this condition, concerning the inhibition of pulmonary vascular remodeling by administering at least one inhibitor of the serotonin transporter (5-HTT).

BACKGROUND AND PRIOR ART

Pulmonary hypertension (referred hereafter as PH) either occurs as a complication of various pathological conditions or is a primary disease for which no underlying cause can be found (Rubin 1997). Persistent vasoconstriction and structural remodeling of the pulmonary vessels are cardinal features of PH (Wagenvoort and Wagenvoort 1970). The origin of this disease, however, remains largely unknown. Evidence was recently provided that serotonin (5-hydroxytryptamine, hereafter referred as 5-HT) plays a major role in the pathogenesis of PH (Herve, Drouet et al. 1990). Indeed, 5-HT causes vasoconstriction through its binding to different types of 5-HT receptors expressed by pulmonary smooth muscle cells, namely 5-$HT_2$ and 5-$HT_{1B/1D}$ receptors (Choi and Maroteaux 1996; MacLean, Sweeney et al. 1996). In addition, 5-HT exerts potent mitogenic and comitogenic effects on pulmonary artery smooth muscle cells (PA-SMCs) which require its internalization by a high affinity and selective transporter (5-HTT) (Lee, Wang et al. 1991; Lee, Wang et al. 1994; Eddahibi, Fabre et al. 1999). The 5-HTT is abundantly expressed in the lung (Ramamoorthy, Bauman et al. 1993) and is the target of appetite suppressant drugs reported to increase the risk of primary PH (Brenot, Herve et al. 1993; Abenhaim, Moride et al. 1996). In recent studies performed on lung tissues and pulmonary arteries from patients with primary PH who underwent lung transplantation, it was discovered that the disease was associated with an increased expression of 5-HTT and a marked enhancement in the proliferative growth responsiveness of cultured PA-SMCs to 5-HT but not to other growth factors (Eddahibi, Humbert et al. 2001). Additional data suggested that the increased expression of 5-HTT in these patients is related to polymorphism of the 5-HTT gene promoter (Eddahibi, Humbert et al. 2001). A role for 5-HTT in experimental hypoxic pulmonary hypertension was also clearly established (Eddahibi, Hanoun et al. 2000). Therefore, 5-HT, notably through its specific transporter, appears as a key component in the pathogenesis of various types of human and experimental PH.

The 5-HTT can be competitively inhibited by specific drugs such as fluoxetine and paroxetine (de Jonghe and Swinkels 1997). Consequently, these drugs inhibit the in vitro proliferative response of SMC to 5-HT and also to a large extent the growth response to serum (Eddahibi, Humbert et al. 2001). However, their effects on PH development have not yet been investigated.

Primary pulmonary hypertension is characterized by increased pulmonary artery pressure and pulmonary vascular resistance. The hemodynamic derangement in primary pulmonary hypertension is an increased resistance to blood flow. Early in the disease the cardiac output is normal, however there is a noticeable elevation in pulmonary artery pressure. With time the cardiac output becomes diminished. At late stages in this disease the pulmonary capillary wedge pressure rises in response to impaired filling of the left ventricle due to an altered configuration of the intraventicular septum. To compensate for the depression in the right ventricular overload, the right atrial end-diastolic pressure rises.

As a result of the depression in the right ventricular septum, gradual onset of shortness of breath occurs in the individual inflicted with pulmonary hypertension. Other common symptoms associated with this disease include fatigue, angina pectoris, syncope, new syncope and peripheral oedema. The survival rate of individuals having pulmonary hypertension is about 2 to 10 years. The cause of death is generally right ventricular failure.

To treat this disease is very difficult. In the past it has been suggested to dramatically limit the individual's exercise coupled with diuretic therapy or vasodilator drugs. However, for example, with vasodilators a reduction in pulmonary vascular resistance may be obtained but in the long run a worsening in the right ventricular function occurs and thereby right ventricular failure occurs over time.

Moreover vasodilators can have acute and chronic adverse side effects. For instance, vasodilators can produce right ventricular ischemia resulting in death of an individual.

Although anticoagulant therapy has been suggested, there is no regression of the disease.

For individuals who have not responded to the radical drug treatment with the above-known vasodilators or anticoagulants, the only solution to the problem is heart-lung transplantation. The survival rate of such an operation is extremely short, i.e., less than 1 year.

Thus, it is an aspect of the present invention to provide a medical solution other than vasodilators, and anticoagulant therapy to prevent, attenuate or treat pulmonary hypertension.

SUMMARY OF THE INVENTION

The present invention is based on the demonstration that administration of a 5-HTT inhibitor to an animal model of pulmonary hypertension can prevent or at least attenuate some symptoms of PH. In particular, it was demonstrated that 5-HTT inhibitors can prevent, treat or at least attenuate right ventricular hypertrophy, proliferation of PA-SMCs, pulmonary vessels muscularization and pulmonary vascular remodeling in mice in hypoxic conditions, while they potentiated the right ventricular systolic pressure increase in response to acute hypoxia.

The invention mainly pertains to a method for preventing, attenuating or treating pulmonary hypertension, comprising administering at least one 5-HTT inhibitor to an individual in need of such treatment.

The invention also pertains to a method for preventing, attenuating or treating an increase in right ventricular systolic pressure (hereafter referred to as RVSP) and/or right ventricular hypertrophy in an individual likely to be subject to pulmonary hypertension, comprising administering at least one 5-HTT inhibitor to said individual in need thereof.

Other aspects of the present invention are methods for preventing, attenuating or attenuating the proliferation of pulmonary artery smooth muscle cells and/or pulmonary vascular remodeling and/or attenuating pulmonary vessels muscularization in an individual likely to be subject to pulmonary hypertension, comprising administering at least one 5-HTT inhibitor to an individual in need thereof.

The invention also concerns a method for increasing vascular tone in an individual under acute hypoxia and in need of such treatment, comprising administering at least one 5-HTT inhibitor which may be useful to improve arterial oxygenation.

A method for increasing vascular tone in an individual under acute hypoxia and in need of such treatment, comprising administering at least one 5-HTT inhibitor to said individual, is also part of the present invention.

Another object of the present invention is a pharmaceutical composition comprising at least one 5-HTT inhibitor and at least one 5-$H_{1B/1D}$ receptor antagonist, in order to treat the PH symptoms.

DETAILED DESCRIPTION OF THE PREFERRED EMBODIMENTS

Figure 1:
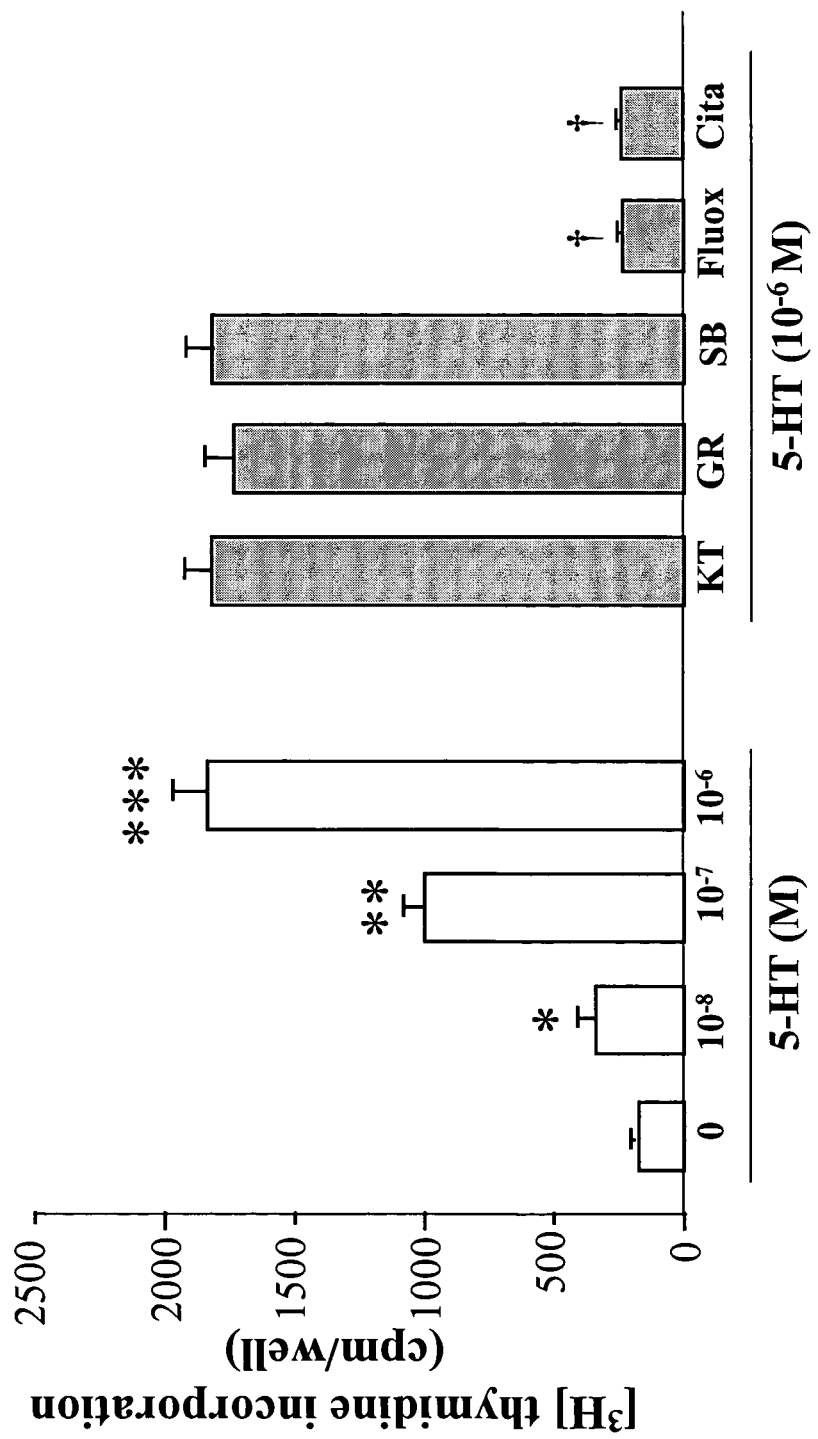
FIG. 1 is a graph showing [$^3$H]Thymidine incorporation in cultured human PA-SMCs in response to increasing concentrations of 5-HT ($10^{-8}$ to $10^{-6}$ M) in the presence of 0.2% FCS. The response was also measured in the presence of ketanserin (KT), SB206553 (SB), GR 127935 (GR), fluoxetine (Fluox) or citalopram (Cita) at $10^{-6}$ M. Values are the means±SEM of six independent experiments. *: P<0.05, : P<0.0.01, *: P<0.001 compared to [$^3$H]Thymidine incorporation with no 5-HT added (0); †: P<0.001 compared to $10^{-6}$ M 5-HT alone.

Throughout this text, the words "prevent", "attenuate" and "treat" should be understood according to the following definitions:

Pulmonary hypertension will be said "prevented" according to the invention if it does not appear. Indeed, some individuals can be considered (for diverse reasons, including genetics) as likely to develop PH, and can undergo a preventing regimen according to the invention, to avoid this disease.

The disease will be "attenuated", or "alleviated", if the symptoms are diminished (in intensity or in frequency), although they do not completely disappear.

In the present text, the disease will be "treated" if the patient is completely cured, which means that the symptoms have disappeared, even if the patient has to continue the treatment to maintain healthy.

Pulmonary vascular remodeling and/or pulmonary vessels muscularization should be understood as an increase of medial thickness of the vascular wall and a reduction in vessel lumen.

Hypoxic pulmonary hypertension (PH) results from both constriction and remodeling of pulmonary vessels and, consequently, offers the opportunity to compare the effects of 5-HTT inhibitors with those of 5-HT receptor antagonists. Indeed, 5-HTT inhibitors can have a selective effect on the proliferation of PA-SMCs whereas 5-HT receptor antagonists can predominantly affect 5-HT-induced pulmonary vasoconstriction. In the experiments described below, the respective roles of 5-HT receptors and 5-HTT on the development of chronic hypoxic PH in the mouse was investigated. For this purpose, animals were treated with either citalopram or fluoxetine, two specific 5-HTT inhibitors (de Jonghe and Swinkels 1997), GR127935, a selective 5-$HT_{1B/1D}$ receptor antagonist (Skingle, Beattie et al. 1996), or ketanserin, a 5-$HT_{2A}$ receptor antagonist (Barnes and Sharp 1999).

As shown in Example 1, it was demonstrated that the mitogenic response of PA-SMCs in culture to 5-HT was abolished by pretreatment of the cells with a 5-HTT inhibitor, while it was not affected by incubation of the cells with any of the receptor antagonists used.

Most importantly, it was shown that administration of a 5-HTT inhibitor to the animal model used for pulmonary hypertension (i.e., mice exposed to hypoxia) resulted in a beneficial effect of the drug on three major symptoms of the disease, namely systolic right ventricular pressure (Example 4.1), right ventricular hypertrophy (Example 4.2), and pulmonary vascular remodeling (Example 4.3).

The invention hence pertains to a method for preventing, attenuating or treating pulmonary hypertension, comprising administering at least one 5-HTT inhibitor to an individual in need thereof. In this method, the 5-HTT inhibitor can be selected amongst fluoxetine, paroxetine, and citalopram or a combination thereof. Of course, any other 5-HTT inhibitor known by the skilled artisan can be used in the method according to the invention, such as, for example, citalopram, fluoxetin, fluvoxamin, paroxetin and sertralin, amineptin, medifoxamin, viloxazin or a combination thereof, as well as combined serotonin and noradrenalin transporter inhibitor.

An example of dosage regimen for using fluoxetine and/or citalopram for treating, preventing or attenuating the symptoms of PH according to the invention is between 0.5 and 10 mg/kg/d.

Other aspects of the present invention are methods for preventing, attenuating or treating an increase in right ventricular systolic pressure (RVSP), right ventricular hypertrophy, proliferation of pulmonary artery smooth muscle cells, pulmonary vascular remodeling, and/or pulmonary vessels muscularization in an individual likely to be subject to pulmonary hypertension, comprising administering at least one 5-HTT inhibitor to said individual. The fact that the subject is "likely to be subject to PH" can be linked to external conditions (for example, if the individual is exposed to a lack of oxygen, as can be the case at very high altitudes, or to a complication of a pathological condition, or to a primary disease.

As discussed below, the treatment according to the above methods can also comprise the administration of at least one antagonist of a 5-HT receptor, especially the $5\text{-}HT_{1B/1D}$ receptor, in addition to the 5-HTT inhibitor. This could help preventing pulmonary vasoreactivity potentiation. An example of $5\text{-}HT_{1B/1D}$ receptor antagonist that can be used in this particular embodiment of the invention is GR127935, which can be administered at a dosage comprised, for example, between 0.2 and 20 mg/kg/d. A pharmaceutical composition comprising at least one 5-HTT inhibitor and at least one $5\text{-}HT_{1B/1D}$ receptor antagonist, is hence another aspect of the present invention. Examples of $5\text{-}HT_{1B/1D}$ receptor antagonists which can be used according to the invention are GR 127935, GR 125743, GR 55562, (Glaxo SmithKline, Harlow, UK), SB 22065 SB 216641, SB 224289, SB 236057 (SmithKline & Bicham) and NAS-181 (Astra).

In the methods according to the invention, the 5-HTT inhibitor can be administered orally. Alternative administration routes can of course be used, depending on the state of the patient. The physician can for example decide that it is preferable to deliver the drug intravenously or in an aerosol, for example.

Surprisingly, the administration of a 5-HTT inhibitor to mice before their exposure to acute hypoxia potentiated the increase of right ventricular systolic pressure (RVSP) in response to hypoxia, whereas a $5\text{-}HT_{1B/1D}$ could abolish this response (Example 2). Therefore, the invention also concerns a method for increasing vascular tone in an individual under acute hypoxia, comprising administering at least one 5-HTT inhibitor to an individual in need thereof. This may be useful to improve arterial oxygenation in patients with lung disease.

While the invention has been described in terms of various preferred embodiments, the skilled artisan will appreciate that various modifications, substitutions, omissions and changes may be made without departing from the scope thereof. Accordingly, it is intended that the scope of the present invention be limited by the scope of the following claims, including equivalents thereof.

Other characteristics of the invention will also become apparent in the course of the description which follows of the biological assays which have been performed in the framework of the invention and which provide it with the required experimental support, without limiting its scope.

EXAMPLES

The experiments described below have been performed using the following materials and methods:

Animal Models and Experimental Design

All experiments were performed using adult male mice (C57BL6/J, 8 weeks old) in conformity with the institutional guidelines that are in compliance with national and international laws and policies.

Hemodynamic Response of Normoxic Mice to Acute Hypoxia

Mice were anaesthetized with ketamine (60 mg/kg, i.p) and xylazine (10 mg/kg, i.p). The trachea was cannulated, and the lungs were ventilated with room air at a tidal volume of 0.2 ml and a rate of 90 breaths per minute. Systemic arterial pressure was determined by catheterization of the carotid artery. A 26-gauge needle was then introduced percutaneously into the right ventricle via the subxyphoid approach. Right ventricular systolic pressure (RVSP) was measured using a Gould P10 EZ pressure transducer connected to pressure modules and a Gould TA 550 recorder. RVSP and heart rate were recorded first while the animal was ventilated with room air and then after 5 min of ventilation with hypoxic gas mixture (8% $O_2$, 92% $N_2$). The heart rate under these conditions was between 300 and 400 bpm. If the heart rate fell below 300 bpm, measurements were excluded from analysis.

Exposure to Chronic Hypoxia

Mice were exposed to chronic hypoxia (10% $O_2$) in a ventilated chamber (500-liter volume, Flufrance, Cachan, France) as previously described (Eddahibi, Hanoun et al. 2000). To establish the hypoxic environment, the chamber was flushed with a mixture of room air and nitrogen, and the gas was recirculated. The chamber environment was monitored using an oxygen analyzer (Servomex OA150, Crowborough, England). Carbon dioxide was removed by soda lime granules, and excess humidity was prevented by cooling the recirculation circuit. The chamber temperature was maintained at 22-24° C. The chamber was opened every other day for 1 hour to clean the cages and replenish food and water supplies. Normoxic mice were kept in the same room, with the same light-dark cycle.

Assessment of Pulmonary Hypertension

Mice previously exposed to hypoxia or room air for 2 weeks were anaesthetized and ventilated with room air as described above. After incision of the abdomen and diaphragm, a 26-gauge needle connected to a pressure transducer was inserted into the right ventricle, and RVSP was recorded immediately. Blood was then sampled for hematocrit determination. Finally, animals were deeply anaesthetized with sodium pentobarbital (40 mg/kg, i.p) and exsanguinated and their thorax was opened to remove lungs and heart. The right ventricle (RV) was dissected from the left ventricle+septum (LV+S), and these dissected samples were weighed.

The lungs were fixed by intratracheal infusion of 4% aqueous buffered formalin at a pressure of 23 cm $H_2O$. The entire specimen was immersed in a bath of the same fixative for one week. A midsagittal slice of the right lung including the apical, azygous and diaphragmatic lobes was processed for paraffin embedding. Sections (5 μm thick) were cut for light microscopy and stained with hematoxylin-phloxin-saffron and orcein-picroindigo-carmine.

In each mouse, a total of 50-60 intraacinar vessels accompanying either alveolar ducts or alveoli were analyzed by an observer blinded to treatment. Each vessel was categorized as nonmuscular (no evidence of any vessel wall muscularization), partially muscular (SMCs identifiable in less than three-fourths of the vessel circumference), or fully muscular (SMCs in more than three-fourths of the vessel circumference). Muscularization was defined as the presence of typical SMCs stained red with phloxin, exhibiting an elongated shape and square-ended nucleus, and bound by two orcein-stained elastic laminae. The percentage of pulmonary vessels in each muscularization category was determined by dividing the number of vessels in that category by the total number counted in the same experimental group.

Pharmacological Treatments

To investigate the effects of 5-HTT inhibition and/or 5-HT receptor blockade on acute hypoxic vasoconstriction, nine groups of mice (6-7 in each group) were studied. Inhibition of 5-HTT was achieved by administration of citalopram or fluoxetine (10 mg/kg/day, in distilled water by gavage) in the first two groups. Two other groups were treated with the 5-HT$_{2A}$ receptor antagonist ketanserin or the 5-HT$_{1B/1D}$ receptor antagonist GR127935 at the same dose of 2 mg/kg/day, i.p. Four additional groups were treated with a combination of one 5-HTT inhibitor and one 5-HT receptor antagonist. The last group consisted of control animals that received distilled water by gavage. The treatments were performed for two days and acute hypoxic vasoconstriction was measured on the following day one hour after the last treatment.

To assess the effect of 5-HTT inhibition and or 5-HT receptor blockade on chronic hypoxia-induced pulmonary hypertension, 6 groups of mice (10-14 in each group) were exposed to chronic hypoxia and treated with either citalopram (10 mg/kg/day), fluoxetine (10 mg/kg/day), ketanserin (2 mg/kg/day), GR127935 (2 and 10 mg/kg/day) or vehicle. An additional group was treated with the combination of fluoxetine (10 mg/kg/day) and GR127935 (2 mg/kg/day). The animals were treated once a day during the two-week exposure to hypoxia.

Effect of 5-HT on the Proliferation of Human Pulmonary Artery Smooth Muscle Cells (PA-SMCs)

The methods used for the culture and the characterization of human PA-SMCs have been previously described (Eddahibi, Humbert et al. 2001). In brief, PA-SMCs were obtained from patients undergoing lung resection for cancer. They were seeded in 24-well plates at a density of $5\times10^4$ cells/well and allowed to adhere in DMEM supplemented with 15% fœtal calf serum (FCS). Cells were then subjected to 48 h of growth arrest in medium containing only 0.2% FCS before being incubated in DMEM supplemented with 0.2% FCS, 0.6 mM of ascorbic acid, 0.1 mM of iproniazid (a monoamine oxidase inhibitor), 0.6 µCi/mL of [$^3$H]thymidine, with or without 5-HT ($10^{-8}$ to $10^{-6}$ M). The effect of 5-HT was also examined in the presence of $10^{-6}$ M of either fluoxetine, citalopram, GR127935, ketanserin or SB206553, a 5-HT$_{2B/2C}$ receptor antagonist (Barnes and Sharp 1999). Each of these drugs was added 20 min before 5-HT. After incubation for 24 hours, cells were washed twice with PBS, treated with ice-cold 10% trichloroacetic acid (1 ml/well), and dissolved in 0.1 N NaOH (0.5 ml/well). The incorporated radioactivity was counted and reported as cpm per well.

Chemicals

[$^3$H]Thymidine was from Amersham Pharmacia Biotech (Buckhingham, UK). Iproniazid, ascorbic acid, 5-HT and SB 206553 (N-3-pyridinyl-3,5-dihydro-5-methyl-benzo[1,2-b:4,5-b']dipyrrole-1(2H)-carboxamide hydrochloride) were from Sigma (St Louis, Mo., USA), Other compounds were fluoxetine (Eli Lilly, Indianapolis, Ind., USA), citalopram (Lundbeck, Copenhagen, DK), ketanserin (Janssen, Beerse, Belgium), GR127935 (2'-methyl-4'-(5-methyl-[1,2,4]oxadiazol-3-yl)-biphenyl-4-carboxylic acid [4-methoxy-3-(4-methyl-piperazine-1-yl)-phenyl]amide, GlaxoSmithKline, Harlow, UK).

Statistical Analyses

All results are expressed as means±SEM.

To compare the effects of pretreatment with 5-HTT inhibitors or 5-HT receptor antagonists on pressure changes caused by acute hypoxia, two-way ANOVA with repeated measurements was performed: significance was tested for pretreatment effect, RVSP under normoxic and hypoxic conditions and interaction. When interaction was significant, Mann-Whitney non parametric test was used to compare the effect of each treatment.

A one-way ANOVA was performed for comparisons of hemodynamic values in mice treated with vehicle or different drugs during continuous exposure to chronic hypoxia. When ANOVA indicated the significance of differences between groups, comparison between two groups was carried out with Scheffe's method. Comparisons of ratios of "right ventricle" (RV) to "left ventricle+septum" (LV+S) weight and hematocrits between the groups were performed using a similar statistical analysis after arcsine transformation of individual values.

To compare the respective degree of muscularization of pulmonary vessels between the various groups of animals, vessels were ordinally classified as nonmuscular (NM), partially muscular (PM) and fully muscular (M) (see above). Comparison of muscularization was performed at both the alveolar duct and wall levels using a non parametric Kruskal-Wallis test. When a significant difference was observed ($P<0.05$), multiple pairwise comparisons were performed with Scheffe's method.

Results

Example 1

Effects of 5-HTT Inhibitors or 5-HT Receptor Antagonists on 5-HT-Induced PA-SMC Proliferation In cells cultured in 0.2% FCS, 5-HT ($10^{-8}$-$10^{-6}$ M) produced a concentration-dependent increase in [$^3$H]thymidine incorporation (FIG. 1). Pretreatment of the cells with fluoxetine ($10^{-5}$ M) or citalopram ($10^{-5}$ M), two 5-HTT inhibitors, completely abolished the 5-HT-induced increase in [$^3$H]thymidine incorporation. In contrast, the mitogenic response to 5-HT was not affected by incubation of the cells with any of the receptor antagonists, GR127935, ketanserin or SB 206553, all tested at $10^{-5}$ M (FIG. 1).

Example 2

Figure 2:
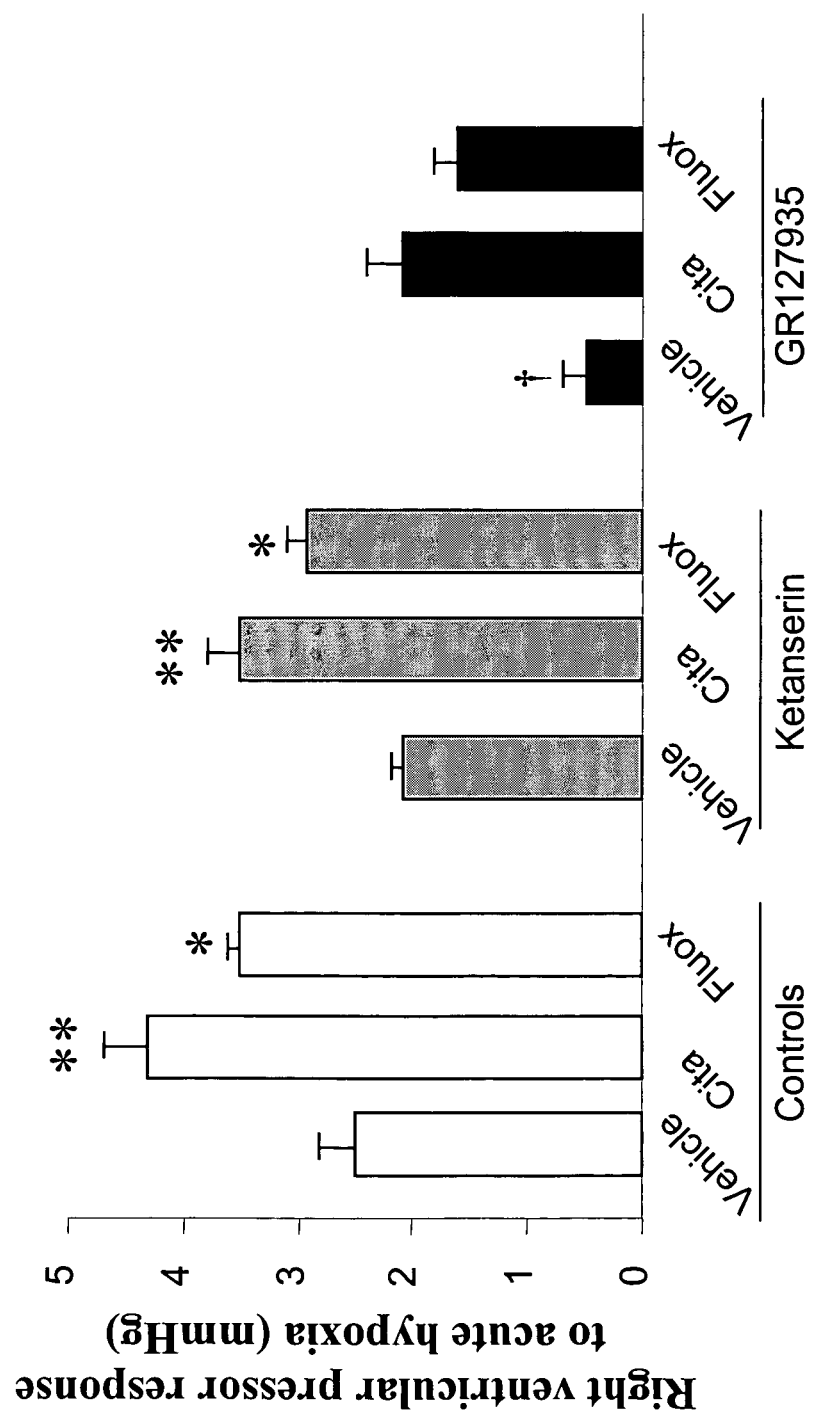
FIG. 2 is a graph showing right ventricular systolic pressure (RSVP) in normoxic mice after 5 min of ventilation with a hypoxic gas mixture (hypoxia). The response was assessed in animals treated for two days with the 5-HTT inhibitor fluoxetine or citalopram, the 5-HT receptor antagonists ketanserin or GR127935 or the combination of each 5-HTT inhibitor and 5-HT receptor antagonist. Baseline RVSP under normoxic ventilation did not differ between groups. *: p<0.05 and **: p<0.01 in comparison with animals exposed to similar acute hypoxic conditions and treated with vehicle (n=6 in each group).

Effects of 5-HTT Inhibitors and 5-HT Receptor Antagonists on Response to Acute Hypoxia Exposure to acute hypoxia (10% $O_2$) induced an increase in RVSP in each of the control mice, reaching a maximum at 5 min. A two-day pretreatment with the 5-HTT inhibitors, citalopram or fluoxetine, did not alter baseline RVSP but potentiated its increase in response to acute hypoxia up to 172% and 142% of the pressure response in vehicle-treated controls, respectively ($P<0.01$ and $P<0.05$, FIG. 2). Similar changes were noted in ketanserin-pretreated mice as this 5-HT$_{2A}$ receptor antagonist altered neither the response to acute hypoxia nor its potentiation by citalopram or fluoxetine (FIG. 2). In contrast, pretreatment with the 5-HT$_{1B/1D}$ receptor antagonist, GR127935, abolished the pressure response to hypoxia, and RVSP in mice which received the combination of GR127935 plus either 5-HTT inhibitor did not differ from that in control mice treated with vehicle only (FIG. 2).

Example 3

Effects of Chronic Treatment with 5-HTT Inhibitors or 5-HT Receptor Antagonists on Physiological Parameters During Normoxia Treatment with either 5-HTT inhibitors or 5-HT receptor antagonists did not alter body weight, heart rate or systemic arterial pressure. Mean systemic arterial pressure, which was 88±7 mmHg in control mice, remained unchanged after treatment with fluoxetine (86±5 mmHg), citalopram (87±7 mmHg), GR127935 (85±6 mmHg), or ketanserin (83±4 mmHg).

Example 4

Effects of 5-HTT Inhibitors and 5-HT Receptor Antagonists on Development of PH 4.1. Systolic Right Ventricular Pressure After a 2-week-exposure to hypoxia (10% $O_2$) associated with daily treatment with citalopram, fluoxetine, GR127935, ketanserin or vehicle, body weight, heart rate and hematocrit did not differ between the corresponding groups of mice (Table 1).

TABLE 1

Body and left ventricular weight, heart rate and hematocrit in mice after a two-week treatment with 5-HTT inhibitor (citalopram, fluoxetine), 5-HT receptor antagonist (ketanserin, GR127935) or vehicle under continuous hypoxia

|  | Vehicle | Citalopram (10 mg/kg/day) | Fluoxetine (10 mg/kg/day) | Ketanserin (2 mg/kg/day) | GR127935 (2 mg/kg/day) | GR127935 (10 mg/kg/day) |
|---|---|---|---|---|---|---|
| Body weight (g) | 22.0 ± 1.3 | 20.5 ± 0.8 | 21.0 ± 1.4 | 21.8 ± 1.0 | 22.2 ± 1.1 | 19.4 ± 1.0 |
| LV + S weight (mg) | 74.2 ± 3.4 | 72.0 ± 4.1 | 73.6 ± 3.2 | 77.1 ± 4.4 | 73.4 ± 3.9 | 74.0 ± 4.8 |
| Heart rate (bpm) | 360 ± 20 | 340 ± 15 | 350 ± 30 | 320 ± 25 | 340 ± 20 | 378 ± 24 |
| Hematocrit (%) | 57 ± 5 | 55 ± 8 | 60 ± 6 | 54 ± 9 | 59 ± 6 | 58 ± 7 |

LV + S = ventricle + septum. No significant difference between groups (one-way ANOVA)

Figure 3A:
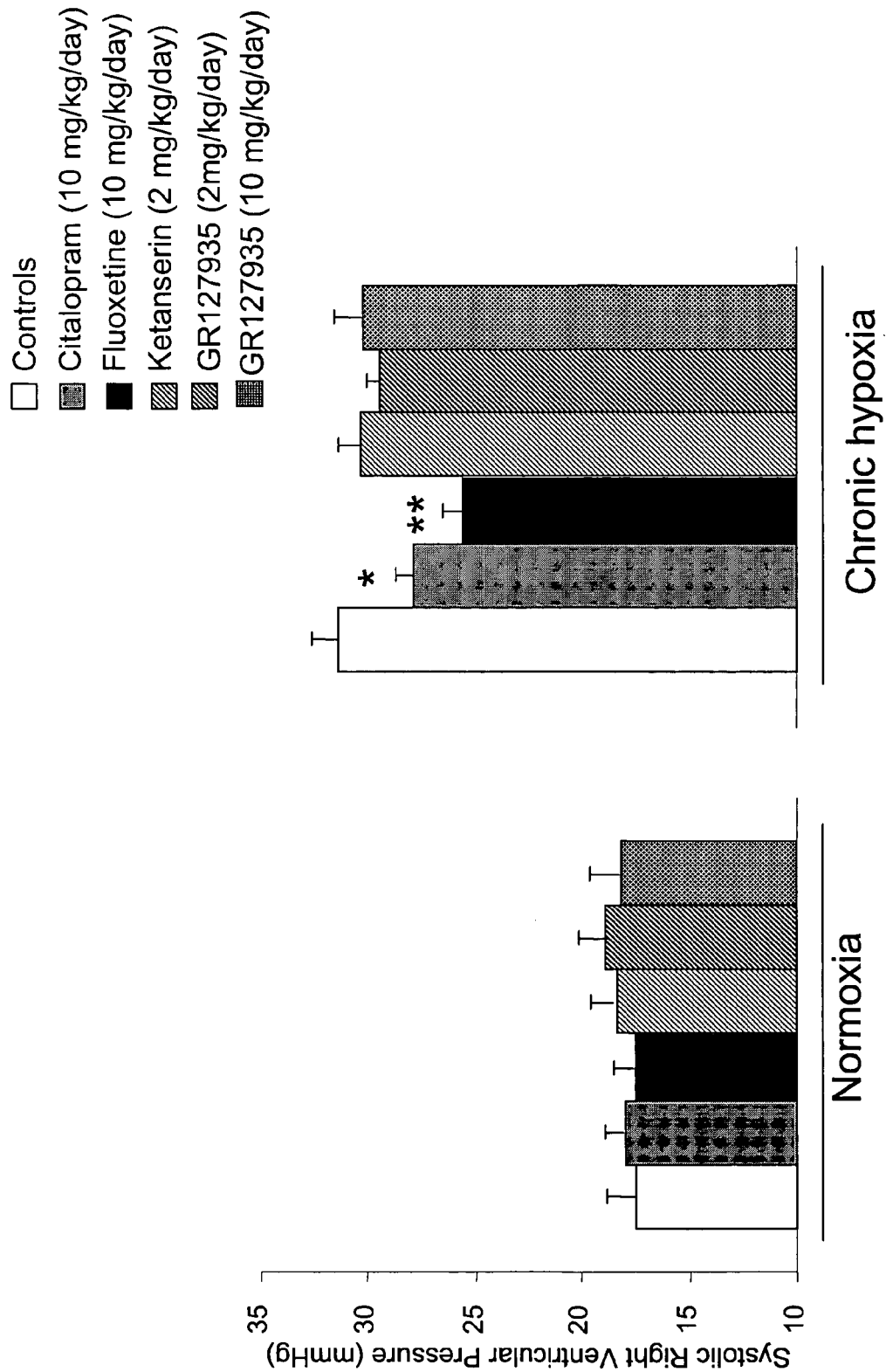
FIG. 3 is a graph showing right ventricular systolic pressure (RVSP) (FIG. 3A) and right ventricle/left ventricle plus septum weight (RV/LV+S) (FIG. 3B) in mice in normoxia or exposed to chronic hypoxia (10% $O_2$) and treated daily with citalopram (10 mg/kg/day), fluoxetine (10 mg/kg/day), ketanserin (2 mg/kg/day), GR127935 (2 and 10 mg/kg/day) or vehicle for two weeks. *: p<0.05, **: p<0.01 as compared with corresponding values in vehicle-treated mice (controls) under similar conditions.
Figure 3B:
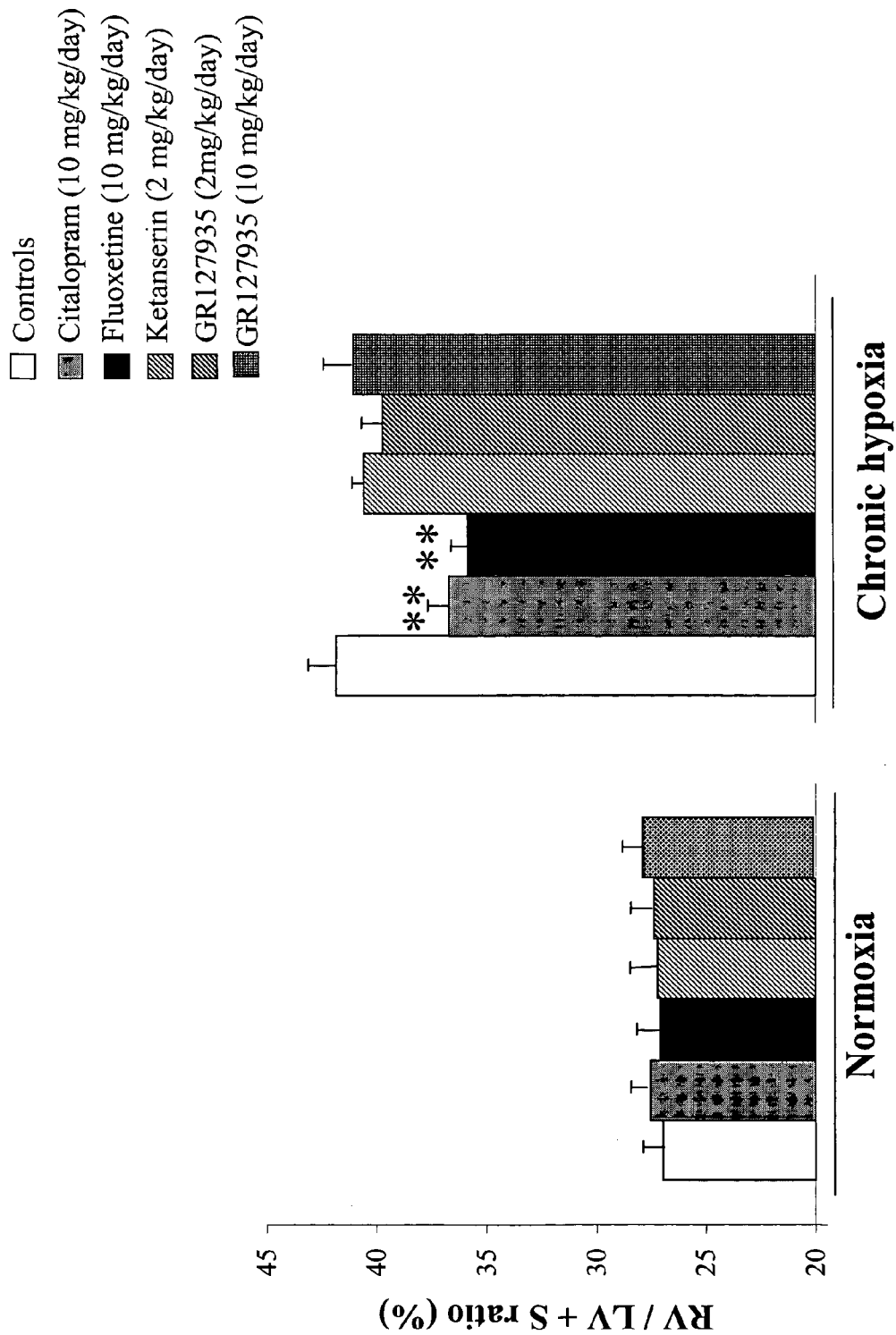

Exposure to hypoxia produced a significant increase in RVSP (31.2±0.6 mm Hg as compared with 17.5±0.7 mm Hg in mice maintained in normoxia, P<0.001). As illustrated in FIG. 3, concomitant treatment with citalopram or fluoxetine significantly attenuated this response, whereas RVSP values in mice that received ketanserin or GR127935 (2 or 10 mg/kg/day) for the whole hypoxic period did not differ from those found in vehicle-treated animals. Under normoxic conditions, none of these treatments affected RVSP (data not shown).

4.2. Right Ventricular Hypertrophy

At the end of exposure to chronic hypoxia, LV+S weight in hypoxic mice did not differ from that measured in mice maintained under normoxic conditions. This result applied whether or not hypoxic animals were treated with fluoxetine, citalopram, ketanserin, GR127935 or vehicle. However, exposure to chronic hypoxia was associated with right ventricular hypertrophy as assessed by the RV/LV+S ratio (41.5±1.5% vs 25.5±1.3%, in hypoxic and normoxic vehicle-treated mice, respectively). As shown in FIG. 3, right ventricular hypertrophy was lower in mice exposed to chronic hypoxia and treated with citalopram or fluoxetine than in animals maintained under similar conditions and receiving vehicle (FIG. 3). In contrast, in mice treated with GR127935 (2 or 10 mg/kg/day) or ketanserin, RV/LV+S ratio did not differ from that measured in hypoxic vehicle-treated mice. Moreover, combined treatment with GR127935 plus fluoxetine had no additional effect on right ventricular hypertrophy than treatment with fluoxetine alone (data not shown).

4.3. Pulmonary Vascular Remodeling

Figure 4:
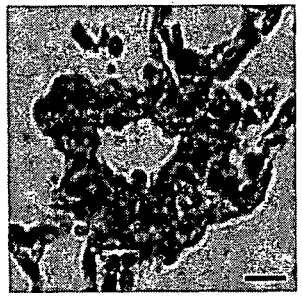
FIG. 4 are photographs showing pulmonary vascular remodeling illustrated by representative photomicrographs of pulmonary vessels from mice exposed to chronic hypoxia and treated with either citalopram, fluoxetine, ketanserin, GR127935 or vehicle for 2 weeks. Sections (5 µm thick) were cut for light microscopy and stained with hematoxylin-phloxin-saffron. Scale bar: 10 µm
Figure 4:
Figure 4:
Figure 4:
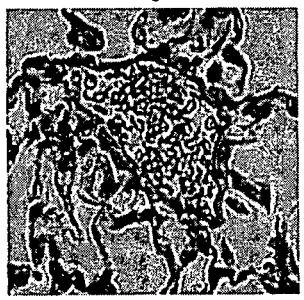
Figure 4:
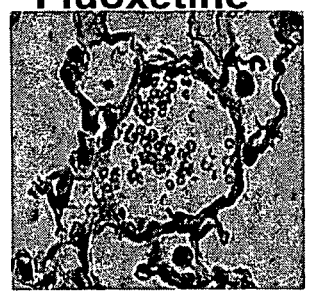
Figure 5:
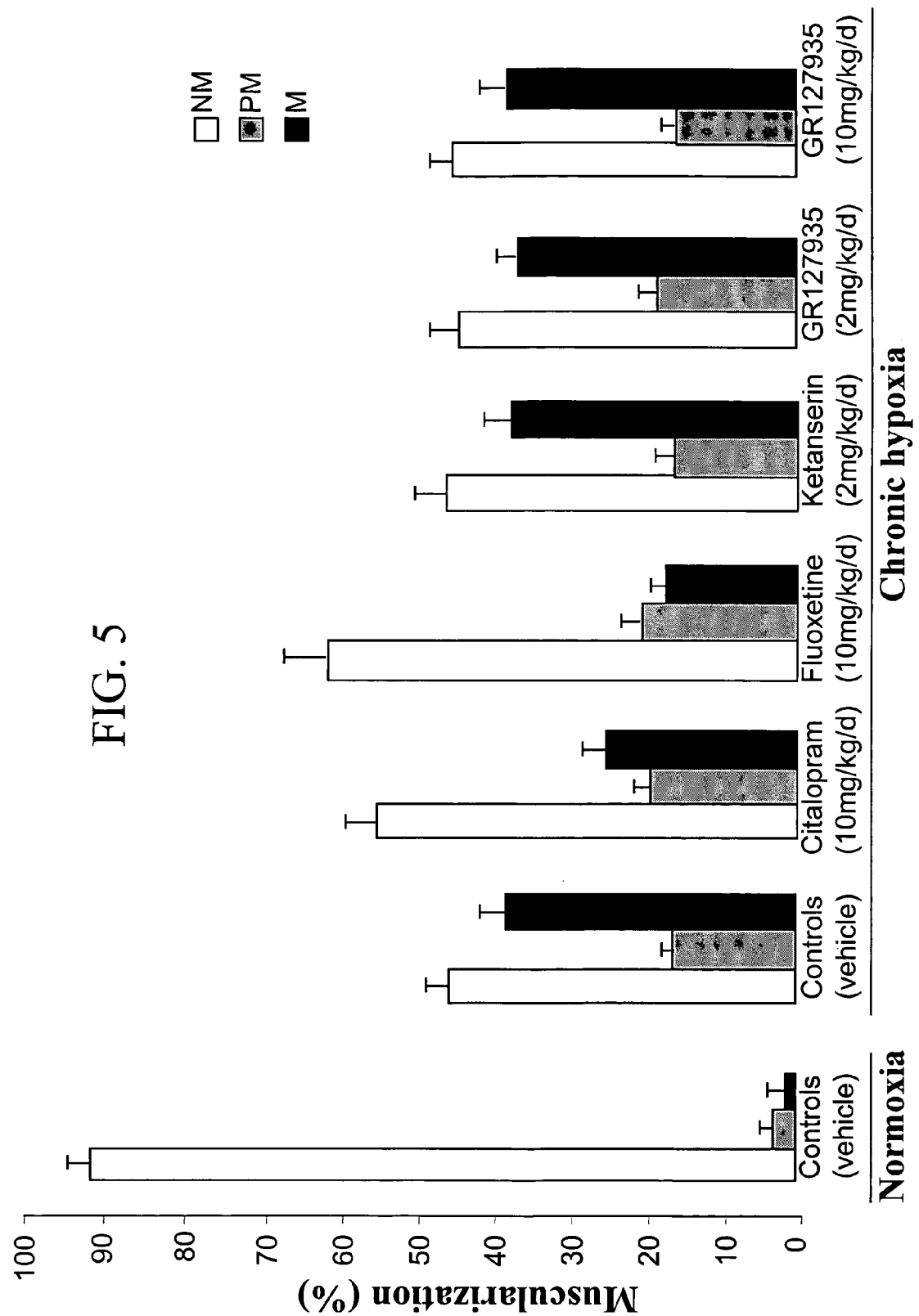
FIG. 5 is a graph showing distribution of vessels according to the accompanying airway. A total of 50-60 intraacinar vessels was analysed in each lung from mice after exposure to hypoxia for 2 weeks and concomitant treatment with vehicle, citalopram (10 mg/kg/day), fluoxetine (10 mg/kg/day), ketanserin (2 mg/kg/day) or GR127935 (2 and 10 mg/kg/day) (n=10 of each group). Percentages of nonmuscular (NM), partially muscular (PM), or fully muscular (M) vessels, determined at the alveolar duct and alveolar wall levels, were lower in citalopram- and in fluoxetine-treated mice than in controls treated by vehicle (P<0.01). There was no difference between GR127935- or ketanserin-treated mice and controls.

In mice exposed to chronic hypoxia and receiving a concomitant treatment with citalopram or fluoxetine, the muscularization of distal pulmonary vessels was markedly attenuated as compared with control mice exposed to similar hypoxic conditions (FIGS. 4 and 5). In contrast, treatment with GR127935 (2 or 10 mg/kg/day) or ketanserin did not affect muscularization in response to hypoxia. Moreover, combined treatment with GR127935 plus fluoxetine did not further decrease muscularization of distal pulmonary vessels than treatment with fluoxetine alone (data not shown).

Discussion

The present results show that antidepressant drugs with selective serotonin transporter inhibitory properties protect against development of hypoxic PH in mice. These drugs impaired hypoxia-induced pulmonary vascular remodeling despite they potentiated acute hypoxic pulmonary vasoconstriction, suggesting that their beneficial effect resulted from their inhibitory action on the proliferation of pulmonary vascular smooth muscle cells. At the opposite, serotonin receptor antagonists, which reduced hypoxic pulmonary vasoconstriction, but did not affect smooth muscle cell proliferation, had no effect on pulmonary vascular remodeling. These results emphasize the fact that structural remodeling of pulmonary blood vessels in response to hypoxia can be reduced independently from an effect on the pulmonary vascular tone and suggest that 5-HTT inhibitors may represent a novel therapeutic approach of pulmonary hypertension.

Hypoxia is a well recognized stimulus for pulmonary blood vessel remodeling. Classically, chronic hypoxic PH is considered as the consequence of vascular remodeling in response to sustained pulmonary vasoconstriction and the subsequent increase in pulmonary artery pressure, that presumably trigger hypertrophy and proliferation of vascular smooth muscle cells. Another mechanism that may be involved in this effect is a direct action of hypoxia on the expression of specific genes controlling SMC proliferation (Yu, Shimoda et al. 1999). Recent studies showed that mice with targeted disruption of the 5-HTT gene (5-HTT knockout mice) develop a lesser degree of hypoxic pulmonary hypertension than wild-type (WT) controls (Eddahibi, Hanoun et al. 2000), suggesting that 5-HTT is a key effector molecule for pulmonary vascular remodeling in response to hypoxia. On the other hand, studies performed with cultured PA-SMCs have previously documented that the 5-HTT mediates the growth promoting effect of serotonin (Lee, Wang et al. 1994; Eddahibi, Fabre et al. 1999; Eddahibi, Humbert et al. 2001), and hypoxia was shown to increase 5-HTT expression and simultaneously stimulate the mitogenic activity of 5-HT (Lee, Dunn et al. 1989; Eddahibi, Fabre et al. 1999). One and/or the other of the two hypoxia-sensitive elements which have been identified in the promoter region of the 5-HTT gene (Eddahibi, Fabre et al. 1999) might participate in the latter events. However, further investigations are needed to answer this question.

The serotonin transporter can be selectively inhibited by antidepressant drugs such as fluoxetine and citalopram (de Jonghe and Swinkels 1997). As previously reported (Eddahibi, Humbert et al. 2001), it was here confirmed that these 5-HTT inhibitors, but not the 5-$HT_{2A}$ receptor antagonist ketanserin, the 5-HT$_{2B/2C}$ receptor antagonist SB 206553 and the 5-HT$_{1B/1D}$ receptor antagonist GR127935, inhibited the mitogenic effect of 5-HT on human PA-SMCs. In addition, as expected from such an effect, it was shown that under hypoxic conditions, mice treated with fluoxetine or citalopram developed less PH than vehicle-treated animals. Not only was the right ventricular systolic pressure lower, but also the right ventricular hypertrophy and pulmonary vessel muscularization were markedly less in 5-HTT inhibitor-treated mice than in vehicle treated controls, suggesting that reduced PA-SMC proliferation caused by this type of antidepressant drug was responsible for the attenuation of PH.

Interestingly, mice treated with either fluoxetine or citalopram showed a potentiated pulmonary pressure response to acute hypoxia as compared with vehicle treated controls. One possible explanation of this phenomenon is that inhibition of 5-HT uptake by platelets or vascular cells allowed more indoleamine to bind to 5-HT receptors on pulmonary SMCs in citalopram- and fluoxetine-treated mice. Indeed, in an earlier study in rats, it was found that 5-HT infusion potentiated the acute pulmonary pressure response to hypoxia (Eddahibi, Raffestin et al. 1997). Moreover, the pulmonary pressure response to hypoxia was also reported to be increased in 5-HTT knock-out mice (Eddahibi, Hanoun et al. 2000). It is therefore reasonable to assume that 5-HT uptake inhibition in fluoxetine- and citalopram-treated mice increases pulmonary vasoreactivity to acute hypoxia through the same mechanism.

The finding that 5-HTT inhibition, on one hand, protected against vascular remodeling, but, on the other hand, increased vascular tone, should be viewed as a physiological paradox. Indeed, in most cases, physiological or pharmacological conditions associated with decreased pulmonary vascular tone protect against PH whereas increased vascular tone has the opposite effect (Kouyoumdjian, Adnot et al. 1994; Eddahibi, Raffestin et al. 1995). It was reasoned that, if increased availability of 5-HT for 5-HT receptors was responsible for the increased vasomotor tone in response to 5-HTT inhibition, treatment with 5-HT receptor antagonists should suppress it and provide an additional benefit. Therefore, they examined the consequence of pharmacological blockade of 5-HT receptors possibly concerned, namely the 5-HT$_{1B}$ and 5-HT$_{2A}$ types, which have previously been shown to mediate pulmonary constriction in response to 5-HT (MacLean, Sweeney et al. 1996). Relevant experiments showed that treatment with the 5-HT$_{1B/1D}$ receptor antagonist GR127935 abrogated acute hypoxic vasoconstriction whereas the 5-HT$_{2A}$ receptor antagonist ketanserin had no effect. In addition, when GR127935 was given in association with citalopram or fluoxetine, the pressor response to acute hypoxia which should have been enhanced by 5-HT uptake blockade was in fact not significantly different from that observed in the absence of drugs. On the other hand, neither GR127935 nor ketanserin affected the development of PH caused by chronic hypoxia, and the combination of GR127935 plus fluoxetine was not more effective than the latter drug alone to reduce this phenomenon. Several conclusions can be drawn from these results. The first one is that precapillary vasoconstriction, which is considered as an important contributor to pulmonary arterial muscularization, may not fully explain the pathophysiology of hypoxic PH. Secondly, SMC proliferation, which represents the main component of pulmonary vascular remodeling, might be viewed as a process unrelated to the amplitude of hypoxic pulmonary vasoconstriction but closely linked to 5-HTT activity. Thirdly, 5-HT$_{1B/1D}$ or 5-HT$_{2A}$ receptors which mediate serotonin-induced constriction of pulmonary vessels appear to be much less effective than 5-HTT in mediating pulmonary vascular remodeling. However, recent studies showed that knock-out mice that do not express 5-HT$_{1B}$ receptors (5-HT$_{1B}$–/–) developed less severe PH and exhibited lower vascular remodeling than wild-type controls (Keegan, Morecroft et al. 2001), suggesting that indeed, 5-HT$_{1B}$ receptors play a role in the development of PH, possibly through 5-HT$_{1B}$ receptor-mediated vasoconstriction by endogenous 5-HT. In these studies performed by Keegan et al (Keegan, Morecroft et al. 2001), treatment with GR127935 was associated with a partial protection against development of PH in rats. The apparent discrepancy between Keegan's data and those described above is probably related to differences in the severity of PH. Indeed, the level of PH exhibited by hypoxic control mice in the present study was more severe than that reported in the Keegan study, with more severe pulmonary vascular remodeling and, probably, a lesser proportional contribution of pulmonary vasoconstriction. Since 5-HT$_{1B}$ receptors mediate 5-HT induced pulmonary vasoconstriction and therefore might alter vascular remodeling through alteration of hypoxic vasoconstriction, it is likely that the high level of pulmonary vascular remodeling obtained in the present study would have favored the action of a drug specifically acting on the process of pulmonary vascular remodeling. Species differences might also play a role. Differences related to the dose of GR127935 are unlikely since GR127935, even tested at high doses (10 mg/kg/day), failed to show more effects than the dose of 2 mg/kg/day, which was already effective in abrogating hypoxic vasoconstriction. Reciprocal interactions between 5-HTT and 5-HT receptors might have also occurred. Indeed, a down regulation of 5-HTT has recently been reported in various brain areas in 5-HTT$_{1B}$–/– mice (Ase, Reader et al. 2001) whereas a down regulation of central 5-HT$_{1B, 1A}$ and $_{2A}$ receptors has been found as adaptive changes in 5-HTT–/– mice (Rioux, Fabre et al. 1999; Fabre, Beaufour et al. 2000). Whether similar changes also occur in lung and possibly account for the decrease in PH development in 5-HTT$_{1B}$–/– (Keegan, Morecroft et al. 2001) and 5-HTT–/– (Eddahibi, Hanoun et al. 2000) mice exposed to chronic hypoxia are relevant question to be addressed in future investigations.

It is noteworthy that the 5-HTT is also the target of appetite suppressant drugs that have been reported to increase the risk of primary PH (Abenhaim, Moride et al. 1996). Dexfenfluramine, like citalopram and fluoxetine, inhibits platelet 5-HT uptake but also exhibits additional effects (Russell and Layerty 2000). In previous studies, treatment with dexfenfluramine was found not to attenuate development of experimental hypoxic PH (Eddahibi, Raffestin et al. 1998). Moreover, discontinuation of a prolonged treatment with dexfenfluramine was associated with an upregulation of 5-HTT and subsequent aggravation of the pulmonary hypertensive process in response to chronic hypoxia (Eddahibi, Adnot et al. 2001). Interestingly, anorectic drugs known or suspected to increase the risk of primary PH, namely, a minorex, fenfluramine, and chlorphentermine, were found to be 5-HTT substrates (Rothman, Ayestas et al. 1999), whereas drugs not reported to be associated with an increased risk of primary PH did not have this property. It has been speculated that drugs that are 5-HTT substrates may be translocated into pulmonary cells where they may cause effects similar to or greater than those of 5-HT. According to this hypothesis, 5-HTT substrates other than 5-HT may also be mitogenic. Support to this proposal has come from a recent study showing that fenfluramine is mitogenic for rat lung SMC and lung fibroblasts (Lee, Wang et al. 2001). It is therefore likely that drugs interacting with 5-HTT might lead to various effects depending on the type of interaction, intrinsic drug toxicity, and individual patient susceptibility.

The above results showing that antidepressant drugs with selective 5-HTT inhibitory properties protect against hypoxia-induced PH may be of important clinical relevance, especially because previous studies demonstrated that 5-HTT overexpression is responsible for pulmonary smooth muscle hyperplasia in patients with primary PH (Eddahibi, Humbert et al. 2001). Indeed, associations linking 5-HTT overexpression to PH and 5-HTT gene polymorphism to susceptibility to PH may exist in various types of PH and 5-HTT inhibition might well represent a novel therapeutic approach of human PH. In the present study, it was demonstrated that fluoxetine and citalopram protected against PA-SMC proliferation but also potentiated in vivo pulmonary vasoreactivity. In patients with PH, this would suggest that selective 5-HTT inhibitors should be given cautiously or in association with 5-HT receptor antagonists.

REFERENCES

Abenhaim, L., Y. Moride, et al. (1996). "Appetite-suppressant drugs and the risk of primary pulmonary hypertension. International Primary Pulmonary Hypertension Study Group." *N End J Med* 335(9): 609-16.

Ase, A. R., T. A. Reader, et al. (2001). "Regional changes in density of serotonin transporter in the brain of 5-HT1A and 5-HT1B knockout mice, and of serotonin innervation in the 5-HT1B knockout." *J Neurochem* 78(3): 619-30.

Barnes, N. M. and T. Sharp (1999). "A review of central 5-HT receptors and their function." *Neuropharmacology* 38(8): 1083-152.

Brenot, F., P. Herve, et al. (1993). "Primary pulmonary hypertension and fenfluramine use." *Br Heart J* 70(6): 537-41.

Choi, D. S. and L. Maroteaux (1996). "Immunohistochemical localisation of the serotonin 5-HT2B receptor in mouse gut, cardiovascular system, and brain." *FEBS Lett* 391(1-2): 45-51.

de Jonghe, F. and J. A. Swinkels (1997). "Selective serotonin reuptake inhibitors-Relevance of differences in their pharmacological and clinical profiles." *CNS Drugs* 7: 452-467.

Eddahibi, S., S. Adnot, et al. (2001). "Dexfenfluramine-associated changes in 5-hydroxytryptamine transporter expression and development of hypoxic pulmonary hypertension in rats." *J Pharmacol Exp Ther* 297(1): 148-54.

Eddahibi, S., V. Fabre, et al. (1999). "Induction of serotonin transporter by hypoxia in pulmonary vascular smooth muscle cells. Relationship with the mitogenic action of serotonin." *Circ Res* 84(3): 329-36.

Eddahibi, S., N. Hanoun, et al. (2000). "Attenuated hypoxic pulmonary hypertension in mice lacking the 5-hydroxytryptamine transporter gene." *J Clin Invest* 105(11): 1555-62.

Eddahibi, S., M. Humbert, et al. (2001). "Serotonin transporter overexpression is responsible for pulmonary artery smooth muscle hyperplasia in primary pulmonary hypertension." *J Clin Invest* 108(8): 1141-50.

Eddahibi, S., B. Raffestin, et al. (1995). "Protection from pulmonary hypertension with an orally active endothelin receptor antagonist in hypoxic rats." *Am J Physiol* 268(2 Pt 2): H828-35.

Eddahibi, S., B. Raffestin, et al. (1998). "Effect of dexfenfluramine treatment in rats exposed to acute and chronic hypoxia." *Am J Respir Crit Care Med* 157(4 Pt 1): 1111-9.

Eddahibi, S., B. Raffestin, et al. (1997). "Treatment with 5-HT potentiates development of pulmonary hypertension in chronically hypoxic rats." *Am J Physiol* 272(3 Pt 2): H1173-81.

Fabre, V., C. Beaufour, et al. (2000). "Altered expression and functions of serotonin 5-HT1A and 5-HT1B receptors in knock-out mice lacking the 5-HT transporter." *Eur J Neurosci* 12(7): 2299-310.

Herve, P., L. Drouet, et al. (1990). "Primary pulmonary hypertension in a patient with a familial platelet storage pool disease: role of serotonin." *Am J Med* 89(1): 117-20.

Keegan, A., I. Morecroft, et al. (2001). "Contribution of the 5-HT(1B) receptor to hypoxia-induced pulmonary hypertension: converging evidence using 5-HT(1B)-receptor knockout mice and the 5-HT(1B/1D)-receptor antagonist GR127935." *Circ Res* 89(12): 1231-9.

Kouyoumdjian, C., S. Adnot, et al. (1994). "Continuous inhalation of nitric oxide protects against development of pulmonary hypertension in chronically hypoxic rats." *J Clin Invest* 94(2): 578-84.

Lee, S. L., J. Dunn, et al. (1989). "Serotonin uptake and configurational change of bovine pulmonary artery smooth muscle cells in culture." *J Cell Physiol* 138(1): 145-53.

Lee, S. L., W. W. Wang, et al. (2001). "Dexfenfluramine as a mitogen signal via the formation of superoxide anion." *Faseb J* 15(7): 1324-5.

Lee, S. L., W. W. Wang, et al. (1994). "Serotonin produces both hyperplasia and hypertrophy of bovine pulmonary artery smooth muscle cells in culture." *Am J Physiol* 266(1 Pt 1): L46-52.

Lee, S. L., W. W. Wang, et al. (1991). "Dual effect of serotonin on growth of bovine pulmonary artery smooth muscle cells in culture." *Circ Res* 68(5): 1362-8.

MacLean, M. R., G. Sweeney, et al. (1996). "5-Hydroxytryptamine receptors mediating vasoconstriction in pulmonary arteries from control and pulmonary hypertensive rats." *Br J Pharmacol* 119(5): 917-30.

Ramamoorthy, S., A. L. Bauman, et al. (1993). "Antidepressant- and cocaine-sensitive human serotonin transporter: molecular cloning, expression, and chromosomal localization." *Proc Natl Acad Sci USA* 90(6): 2542-6.

Rioux, A., V. Fabre, et al. (1999). "Adaptive changes of serotonin 5-HT2A receptors in mice lacking the serotonin transporter." *Neurosci Lett* 262(2): 113-6.

Rothman, R. B., M. A. Ayestas, et al. (1999). "A minorex, fenfluramine, and chlorphentermine are serotonin transporter substrates. Implications for primary pulmonary hypertension." *Circulation* 100(8): 869-75.

Rubin, L. J. (1997). "Primary pulmonary hypertension." *N End J Med* 336(2): 111-7.

Russell, B. R. and R. Layerty (2000). "Correlation between 5-HT content and uptake site density following (S)-MDMA and dexfenfluramine-induced depletion, and with neuroprotection by the glycine site-specific NMDA antagonist ACEA 1021." *Ann N Y Acad Sci* 914: 208-14.

Skingle, M., D. T. Beattie, et al. (1996). "GR127935: a potent and selective 5-HT1D receptor antagonist." *Behav Brain Res* 73(1-2): 157-61.

Wagenvoort, C. A. and N. Wagenvoort (1970). "Primary pulmonary hypertension. A pathologic study of the lung vessels in 156 clinically diagnosed caes." *Circulation* 42: 1163-71.

Yu, A. Y., L. A. Shimoda, et al. (1999). "Impaired physiological responses to chronic hypoxia in mice partially deficient for hypoxia-inducible factor 1alpha." *J Clin Invest* 103(5): 691-6.

The invention claimed is:

1. A method for attenuating or treating pulmonary hypertension in an individual in need thereof, comprising administering at least one 5-HTT inhibitor selected from the group consisting of fluoxetine, paroxetine, citalopram and a combination thereof at a dose of between 1 and 100 mg/kg/d and GR127935 as a 5-HT$_{1B/1D}$ receptor antagonist to said individual, wherein GR127935 is administered at a dose of between 0.2 and 20 mg/kg/d, and wherein GR127935 is administered to reverse the potentiated vasoconstrictive effects induced by the administration of said 5-HTT inhibitor.

2. The method of claim 1, wherein said at least one 5-HTT inhibitor is administered orally.

3. A method for attenuating or treating an increase in right ventricular systolic pressure (RVSP) in an individual likely to be subject to pulmonary hypertension, comprising administering at least one 5-HTT inhibitor selected from the group consisting of fluoxetine, paroxetine, citalopram and a combination thereof at a dose of between 1 and 100 mg/kg/d and GR127935 as a 5-HT$_{1B/1D}$ receptor antagonist to said individual in need thereof, wherein GR127935 is administered at a dose of between 0.2 and 20 mg/kg/d.

4. A method for attenuating or treating right ventricular hypertrophy in an individual likely to be subject to pulmonary hypertension, comprising administering at least one 5-HTT inhibitor selected from the group consisting of fluoxetine, paroxetine, citalopram and a combination thereof at a dose of between 1 and 100 mg/kg/d and GR127935 as a 5-HT$_{1B/1D}$ receptor antagonist to an individual in need thereof, wherein GR127935 is administered at a dose of between 0.2 and 20 mg/kg/d.

5. A method for attenuating pulmonary vascular remodeling in an individual likely to be subject to pulmonary hypertension and in need of such treatment, comprising administering at least one 5-HTT inhibitor selected from the group consisting of fluoxetine, paroxetine, citalopram and a combination thereof at a dose of between 1 and 100 mg/kg/d and GR127935 as a 5-HT$_{1B/1D}$ receptor antagonist to said individual, wherein GR127935 is administered at a dose of between 0.2 and 20 mg/kg/d.

6. A method for attenuating pulmonary vessels muscularization in an individual likely to be subject to pulmonary hypertension and in need of such treatment, comprising administering at least one 5-HTT inhibitor selected from the group consisting of fluoxetine, paroxetine, citalopram and a combination thereof at a dose of between 1 and 100 mg/kg/d and GR127935 as a 5-HT$_{1B/1D}$ receptor antagonist to said individual, wherein GR127935 is administered at a dose of between 0.2 and 20 mg/kg/d.

7. A method for attenuating or treating pulmonary hypertension in an individual in need thereof comprising administering a 5-HTT inhibitor selected from the group of fluoxetine, paroxetine and citalopran at a dose of between 1 and 100 mg/kg/d and GR127935 at a dose of between 0.2 and 20 mg/kg/d, wherein GR127935 is administered to reverse the potentiated vasoconstrictive effects induced by the administration of said 5-HTT inhibitor.

* * * * *